United States Patent [19]

Stüber et al.

[11] Patent Number: 5,478,810
[45] Date of Patent: Dec. 26, 1995

[54] PEPTIDE AMIDES, PROCESSES FOR THE PREPARATION THEREOF AND AGENTS CONTAINING THESE AS FIBRIN/THROMBIN CLOTTING INHIBITORS

[75] Inventors: Werner Stüber, Lahntal; Karl Fickenscher, Marburg, both of Germany

[73] Assignee: Behringwerke Aktiengesellschaft, Marburg, Germany

[21] Appl. No.: 22,381

[22] Filed: Feb. 24, 1993

Related U.S. Application Data

[63] Continuation of Ser. No. 696,085, May 6, 1991, abandoned.

[30] Foreign Application Priority Data

May 8, 1990 [DE] Germany ............... 40 14 655.3

[51] Int. Cl.$^6$ ............... C07K 7/06; A61K 38/00
[52] U.S. Cl. ............... 514/17; 530/329; 530/330
[58] Field of Search ............... 530/329, 330; 514/17

[56] References Cited

FOREIGN PATENT DOCUMENTS 3811647A 10/1989 Germany.

OTHER PUBLICATIONS

Hsei et al., J. Med. Chem 24:322–327 (1981).
Chemical Abstracts, 113:172426m (1990).
Chemical Abstracts, 107:215362h (1987).
Chemical Abstracts, 115:109014b (1991).
European Search Report dated Mar. 3, 1992 for Application No. EP 91107307.
Plow, et al Proc. Natl. Acad. Sci 79, (1982) pp. 3711–3715.
Chemical Abstracts, vol. 113 (19) 172426M.
Laudano, et al., Proc. Natl. Acad. Sci. USA, vol. 75 (1978) pp. 3085–3089.
Root–Bernstein, et al., Proc. Natl Acad Sci. USA 81 (1984) pp. 4339–4342.
Stuber et al., Int. J. Peptide Protein Res., 34, 215–221 (1989).

Primary Examiner—Jill Warden
Assistant Examiner—S. G. Marshall
Attorney, Agent, or Firm—Finnegan, Henderson, Farabow, Garrett & Dunner

[57] ABSTRACT

Peptide amides of the formula I (SEQ ID NOS: 3–21)

$$\text{GPRP—X—NR}_1\text{—R}_2 \qquad \text{I}$$

where G is the amino acid glycine, P is the amino acid L-proline, R is the amino acid L-arginine, X is a proteinogenous amino acid apart from proline or a dipeptide from these amino acids including proline, N is nitrogen and $R_1$ and $R_2$ are identical or different and are hydrogen or a lower alkyl chain having up to 4 carbon atoms; processes for the preparation thereof and the use thereof as medicament or for diagnostic purposes are described.

6 Claims, No Drawings

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly Pro Arg Pro
    1

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Gly Pro Arg Pro Pro
    1               5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Gly Pro Arg Pro Ala
    1               5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gly Pro Arg Pro Ser
    1               5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
    Gly   Pro   Arg   Pro   Lys
    1                       5
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
    Gly   Pro   Arg   Pro   Phe
    1                       5
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
    Gly   Pro   Arg   Pro   Gly
    1                       5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
    Gly   Pro   Arg   Pro   Trp
    1                       5
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
    Gly   Pro   Arg   Pro   Tyr
    1                       5
```

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

```
    Gly   Pro   Arg   Pro   Val
    1                       5
```

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:11:

Gly Pro Arg Pro Ile
    1                5

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:12:

Gly Pro Arg Pro Asp
    1                5

(2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:13:

Gly Pro Arg Pro Glu
    1                5

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:14:

Gly Pro Arg Pro Gly
    1                5

(2) INFORMATION FOR SEQ ID NO:15:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:15:

Gly Pro Arg Pro Ser
    1                5

(2) INFORMATION FOR SEQ ID NO:16:

(i) SEQUENCE CHARACTERISTICS:
        (A) LENGTH: 6 amino acids (B) TYPE: amino acid
(D) TOPOLOGY: linear (ii) MOLECULE TYPE: peptide (xi) SEQUENCE DESCRIPTION: SEQ ID NO:16:

Gly Pro Arg Pro Pro Pro
1               5

(2) INFORMATION FOR SEQ ID NO:17:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (xi) SEQUENCE DESCRIPTION: SEQ ID NO:17:

Gly Pro Arg Pro Gly Gly
1               5

(2) INFORMATION FOR SEQ ID NO:18:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (xi) SEQUENCE DESCRIPTION: SEQ ID NO:18:

Gly Pro Arg Pro Pro Arg
1               5

(2) INFORMATION FOR SEQ ID NO:19:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (xi) SEQUENCE DESCRIPTION: SEQ ID NO:19:

Gly Pro Arg Pro Arg Pro
1               5

(2) INFORMATION FOR SEQ ID NO:20:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (xi) SEQUENCE DESCRIPTION: SEQ ID NO:20:

Gly Pro Arg Pro Ala Gly
1               5

(2) INFORMATION FOR SEQ ID NO:21:

(i) SEQUENCE CHARACTERISTICS:
    (A) LENGTH: 6 amino acids
    (B) TYPE: amino acid
    (D) TOPOLOGY: linear (ii) MOLECULE TYPE: peptide (xi) SEQUENCE DESCRIPTION: SEQ ID NO:21:

Gly Pro Arg Pro Gly Gly
1               5

(2) INFORMATION FOR SEQ ID NO:22:

(i) SEQUENCE CHARACTERISTICS:
     (A) LENGTH: 5 amino acids
     (B) TYPE: amino acid
     (D) TOPOLOGY: linear (ii) MOLECULE TYPE: peptide (xi) SEQUENCE DESCRIPTION: SEQ ID NO:22:

Gly Lys Arg Pro Gly
1               5

PEPTIDE AMIDES, PROCESSES FOR THE PREPARATION THEREOF AND AGENTS CONTAINING THESE AS FIBRIN/THROMBIN CLOTTING INHIBITORS

This application is a continuation of application Ser. No. 07/696,085, filed May 6, 1991, now abandoned.

The invention relates to oligopeptide amides and processes for the preparation thereof. The described compounds are capable of preventing the formation of clots in the blood, i.e. blood coagulation. For this reason, these peptides are of therapeutic and diagnostic interest.

According to the state of the art, compounds are known which are capable of inhibiting blood clotting. Inter alia, peptide derivatives and proteins are such substances. In particular antithrombin III, which is used in therapy, and peptide chloromethyl ketones, which are used in diagnosis, belong to this group. The efficacy of these substances is based on the inhibition of thrombin, that is to say fibrinogen is no longer degraded to give fibrin, and F XIII is not activated. However, for various diagnostic purposes it is of interest to activate fully the blood clotting cascade with the formation of thrombin, or to add thrombin directly to the test mixture, but without allowing a clot to form. This means that clotting inhibitors have to be used which are capable of preventing fibrin, which has already been formed by thrombin, from forming a clot.

For therapeutic purposes it is of interest to prevent the formation of a fibrin clot in the presence of soluble fibrin. This is the case, for example, in the prevention of arteriole occlusion in the case of disseminated intravascular coagulation, or when preventing a re-formation of a fibrin clot in a lysine therapy while the local activation of clotting is maintained.

As has been shown in German Patent 3,811,647, a test system for blood clotting factor XIII can be established by adding a clotting inhibitor. The added clot inhibitor does not inhibit thrombin, but does prevent the association of soluble fibrin chains. The peptide used has the peptide sequence (SEQ ID NO: 1) Gly—Pro—Arg—Pro. However, it is a disadvantage that a relatively large amount of this peptide has to be added to avoid clotting completely. The same is also true for the therapeutic use of this tetrapeptide.

At the XIth American Symposium on Peptides (July 1989) a number of other active peptide derivatives was presented (abbreviations are explained further below):

| Structure | relative activity (amount of plasma which is inhibited with a defined amount of inhibitor) |
|---|---|
| GPRP (SEQ ID NO: 1) | 1 |
| GPRP 4-hydroxypiperidide (SEQ ID NO: 1) | 1.2 |
| GPRP 3-methylpiperidide (SEQ ID NO: 1) | 1.29 |
| GPRP-NH$_2$ (SEQ ID NO: 1) | 3.52 |
| GPRPP-NH$_2$ (SEQ ID NO: 2) | 4.56 |

The increase in the action of the peptides shown is based on the incorporation of cyclic amine derivatives as C-terminal building block.

It was the object of the present invention to find peptides which are even more active in comparison with the state of the art.

The invention therefore relates to peptide amides of the formula I (SEQ ID NO: 3–21)

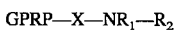

where G is the amino acid glycine, P is the amino acid L-proline, R is the amino acid L-arginine, X is a proteinogenous amino acid apart from proline or a dipeptide from these amino acids including proline, N is nitrogen and $R_1$ and $R_2$ are identical or different and are hydrogen or a lower alkyl chain having up to 4 carbon atoms.

The following peptides are mentioned as examples:
GPRPA—NH$_2$ (SEQ ID NO: 3), GPRPS—NH$_2$ (SEQ ID NO: 4), GPRPK—NH$_2$ (SEQ ID NO: 5), GPRPF—NH$_2$ (SEQ ID NO: 6), GPRPG—NH$_2$ (SEQ ID NO: 7), GPRPW—NH$_2$ (SEQ ID NO: 8), GPRPY—NH (SEQ ID NO: 9), GPRPV—NH$_2$ (SEQ ID NO: 10), GPRPI—NH$_2$ (SEQ ID NO: 11), GPRPD—NH$_2$ (SEQ ID NO: 12), GPRPE—NH$_2$ (SEQ ID NO: 13), GPRPG—NH(ethyl) (SEQ ID NO: 14), GPRPG—N(ethyl)$_2$ (SEQ ID NO: 14), GPRPS—NH(isopropyl) (SEQ ID NO: 15), GPRPW—N(methyl)$_2$ (SEQ ID NO: 8), GPRPG—NH(butyl) (SEQ ID NO: 14), GPRPPP—NH$_2$ (SEQ ID NO: 16), GPRPGG—NH$_2$ (SEQ ID NO: 17), GPRPPR—NH$_2$ (SEQ ID NO: 18), GPRPRP—NH$_2$ (SEQ ID NO: 19), GPRPPP—NH(isopropyl) (SEQ ID NO: 16), GPRPAG—NH$_2$ (SEQ ID NO: 20) and GPRPGG—NH$_2$ (SEQ ID NO: 21).

The amino acids whose stereoform has not been defined above are preferably present in the L-form but may also be present in the D-form.

The peptide derivatives according to the invention are prepared by methods known per se, the solid phase method having been used for the synthesis of the nonalkylated amides ($R_1$ and $R_2$ are hydrogen). Preferably, the procedure described in Int. J. Peptide Protein Res. 34, 215–221, 1989 was used in this case.

The peptides were preferably synthesized on 1% crosslinked polystyrene/divinylbenzene copolymer which was derivatized with an acid-labile amide anchor functionality. The initial amino group formation was in the region of 0.3–0.8 mmol/g of resin.

The synthesis was carried out with repetitive coupling of the individual protected amino acids from the C- to the N-terminus of the peptide. In accordance with their chemical structure, the amino acids are protected on the N-alpha-nitrogen and, if appropriate, on the third functionality. The nitrogen functionalities (N-alpha) were protected by means of the Fmoc group, alcoholic side groups as tert.-butyl ether, carboxyl groups in the side chain as tert.-butyl ester and the guanidine group by means of the Mtr or Pmc group.

The synthesis of the peptides was, in this case, carried out on a semiautomatic or fully automatic peptide synthesizer, comprising the following steps:

wash resin (15 ml/g of resin) solvent DMF (or dichloromethane or N-methylpyrrolidone)

cleave off the Fmoc group using 20% piperidine in DMF wash the resin with DMF (or N-methylpyrrolidone)

couple on the amino acid by using a condensing agent such as carbodiimide, if appropriate adding HOBt or using a mixed or symmetrical anhydride or an active ester instead of this.

after coupling is complete, wash out the excess reagents (DMF).

A Boc-amino acid was normally used as last amino acid. The peptide was then cleaved off using a mixture of trifluoroacetic acid, preferably 90%, and in the presence of a scavenger, such as ethanedithiol, water, resorcinol, anisole or thioanisole, individually or as a scavenger mixture at room temperature or at temperatures up to 40 degrees in the course of 1–2 hours.

The peptides were crystallized by precipitation in an ether and purified by gel permeation. The purity of the peptides was determined by HPLC and amino acid analysis.

The penta- and hexapeptide alkylamides were synthesized by the classical method which takes place in solution. First the protected (Boc- or Z-) amino acid was coupled to the appropriate alkylamine, using the same methods as in the solid phase method. The intermediate products were, depending on their physical characteristics, purified by recrystallization, extraction and reprecipitation. After cleaving off the N-terminal protecting group, in the case of Boc by acidolysis using 1.2 N HCl in glacial acetic acid or using 50% TFA in dichloromethane, and in the case of Z by hydrogenolysis, the next amino acid is coupled on as has already been described. In the case of arginine, normally no protecting group was used on the guanidino group which was merely protonated.

After final deprotection, the peptides were purified in a customary way. For this purpose, gel permeation and, as an exception, also HPLC purification on RP-18 material were suitable methods. The compounds were analyzed for homogeneity and structure using HPLC and amino acid analysis and $^{13}$C-NMR spectroscopy.

The peptides according to the invention were also tested for their inhibitory capability. For this purpose, inhibitor was added to a plasma sample and, after adding thrombin, the time until the sample had clotted was determined. A representative result is detailed in the examples.

As can be seen therefrom, the peptides according to the invention have markedly increased inhibitory potentials in comparison with the known compounds.

In the case of the pentapeptide amides, it has surprisingly been found here that especially small amino acids such as glycine and alanine are advantageous as C-terminal amino acid. However, according to the state of the art cyclic structures such as proline or piperidine derivatives are preferred here.

| Abbreviations: | |
|---|---|
| Ala = A | alanine |
| Asp = D | aspartic acid |
| Asn = N | asparagine |
| Gly = G | glycine |
| Val = V | valine |
| Leu = L | leucine |
| Ile = I | isoleucine |
| Ser = S | serine |
| Thr = T | threonine |
| Met = M | methionine |
| Pro = P | proline |
| Lys = K | lysine |
| Arg = R | arginine |
| Glu = E | glutamic acid |
| Gln = Q | glutamine |
| Phe = F | phenylalanine |
| Tyr = Y | tyrosine |
| Trp = W | tryptophan |
| HOBt | hydroxybenzotriazole |
| DIC | diisopropylcarbodiimide |
| TFA | trifluoroacetic acid |
| Z | benzyloxycarbonyl |
| Boc | butyloxycarbonyl |
| Fmoc | fluorenylmethyloxycarbonyl |
| Pmc | pentamethylchromansulfonyl |

| -continued | |
|---|---|
| Abbreviations: | |
| DMF | dimethylformamide |

The following example illustrates the invention in more detail:

EXAMPLE

Preparation of (SEQ ID NO: 3) Gly—Pro—Arg—Pro—Ala—NH$_2$ 1 g of Fmoc-amide anchor resin (0.47 mmol of amino groups/gram) was washed 3 times with 15 ml of DMF, and the Fmoc group was cleaved off with 20 % piperidine in DMF (1×3 min; 1×10 min). The resin was washed twice in each case with DMF and isopropanol. Thereafter, 2 mmol of Fmoc-Ala were incubated with 3 mmol of HOBt and 2.2 mmol of DIC in 15 ml of DMF together with the resin for one hour. Excess reagents were then filtered off and the resin was washed twice in each case with DMF and isopropanol. Using a ninhydrin test, the completeness of the conversion was checked and, if it was not complete, the coupling was repeated. This method was also used for coupling on the other amino acids. In the case of Arg, the Pmc protecting group was used. A Boc-amino acid was used as last amino acid. The peptide-resin was washed with methanol and diethyl ether and dried in vacuo. The resin was treated with 20 ml of a mixture of 90% TFA and 10% ethanedithiol at 35° C. for 1 hour. The dissolved peptide was crystallized in ether and chromatographed on $^R$Sephadex-G25 in 0.5% acetic acid. The pooled peptide was freeze-dried and, according to HPLC, was 95% pure. The amino acid analysis showed a peptide content of 68%.

TESTING 100 microliters of the clotting inhibitor (peptide) in various concentrations were added to 25 microliters of plasma. The conversion of the fibrinogen to fibrin was initiated by adding 25 microliters of thrombin (50 IU/ml). The clotting of the mixture was monitored by measuring the cloudiness on a clotting analyzer (ACL 300 connected to a computer).

In a second mixture, 50 microliters of the peptide solution and 50 microliters of thrombin solution were, in each case, added to 100 microliters of plasma, and measured as above. The start of clotting was regarded as that point in time at which the scattered light had increased by the same amount as defined by the manufacturer of the device (Instrumentation Laboratory, Milan) for the determination of the prothrombin time in the case of plasma samples.

All the peptides specified are peptide amides ($R_1$=$R_2$=H). The values listed are clotting times in seconds.

| Test mixture I: | 100 µl of clot inhibitor |
| | 25 µl of plasma |
| | 25 µl of thrombin |

| Concentration of clot inhibitor | Clotting time in seconds | | | | | |
|---|---|---|---|---|---|---|
| mg/ml | 2 | 1 | 0.5 | 0.25 | 0.125 | 0.06 |
| Peptide amide | | | | | | |

-continued

Test mixture I: 100 µl of clot inhibitor
25 µl of plasma
25 µl of thrombin

| Concentration of clot inhibitor mg/ml | Clotting time in seconds | | | | | |
|---|---|---|---|---|---|---|
| | 2 | 1 | 0.5 | 0.25 | 0.125 | 0.06 |
| GPRPPP (SEQ ID NO: 16) | 592.2 | 498.1 | 201.7 | 76.3 | 28.8 | 21.2 |
| GPRPG (SEQ ID NO: 7) | 999.9 | 718.5 | 229.3 | 73.5 | 27.9 | 20.3 |
| GPRPPR (SEQ ID NO: 18) | 493.4 | 310.9 | 109.6 | 66.8 | 30.7 | 21.2 |
| GPRPRP (SEQ ID NO: 19) | 574.1 | 617.8 | 205.5 | 79.2 | 32.6 | 21.2 |
| GPRPA (SEQ ID NO: 3) | 635.9 | 535.0 | 300.5 | 148.5 | 51.6 | 24.1 |
| GPRPD (SEQ ID NO: 12) | 430.7 | 166.6 | 45.9 | 22.2 | 20.3 | 21.2 |
| GPRPW (SEQ ID NO: 8) | 879.1 | 726.1 | 190.3 | 70.6 | 26.9 | 20.3 |
| GPRPK (SEQ ID NO: 5) | 258.1 | 139.9 | 173.2 | 102.0 | 51.6 | 25.0 |
| GPRPS (SEQ ID NO: 15) | 115.3 | 114.3 | 83.3 | 41.2 | 23.1 | 20.3 |
| GPRP (SEQ ID NO: 1) | 494.3 | 181.8 | 48.8 | 23.1 | 20.3 | 20.3 |
| GPRPP (SEQ ID NO: 2) | 699.5 | 425.9 | 228.3 | 73.5 | 28.8 | |
| GPRPV (SEQ ID NO: 10) | 174.2 | 225.5 | 148.5 | 83.0 | 32.6 | |
| GPRPI (SEQ ID NO: 11) | 785.0 | 968.4 | 181.8 | 57.3 | 25.9 | |
| GPRPF (SEQ ID NO: 6) | 482.9 | 196.0 | 88.7 | 33.6 | 21.2 | |
| GPRPAG (SEQ ID NO: 20) | 201.7 | 191.3 | 142.8 | 84.9 | 33.6 | |
| GLRPG (SEQ ID NO: 22) | 25.0 | 25.0 | 25.0 | 24.1 | 24.1 | |

Test mixture II: 50 µl of clot inhibitor
100 µl of plasma
50 µl of thrombin

| Concentration of clot inhibitor mg/ml | Clotting time in seconds | | | | | |
|---|---|---|---|---|---|---|
| | 2 | 1 | 0.5 | 0.25 | 0.125 | 0.06 |
| Peptide amide | | | | | | |
| GPRPPP (SEQ ID NO: 16) | 316.7 | 61.1 | — | 19.3 | 19.3 | 20.3 |
| GPRPG (SEQ ID NO: 7) | 126.7 | 43.1 | 20.3 | 18.4 | 19.3 | 19.3 |
| GPRPPR (SEQ ID NO: 18) | 89.6 | 32.6 | 19.3 | 18.4 | 19.3 | 19.3 |
| GPRPRP (SEQ ID NO: 19) | 106.7 | 36.4 | 19.3 | 18.4 | 19.3 | 19.3 |
| GPRPA (SEQ ID NO: 3) | 448.7 | 83.9 | 25.9 | 19.3 | 19.3 | 19.3 |
| GPRPD (SEQ ID NO: 12) | 350.9 | 48.8 | 47.8 | 19.3 | 20.3 | 20.3 |
| GPRPW (SEQ ID NO: 8) | 85.8 | 25.0 | 19.3 | 19.3 | 19.3 | 20.3 |
| GPRPK (SEQ ID NO: 5) | 113.4 | 35.5 | 19.3 | 18.4 | 19.3 | 19.3 |
| GPRPS (SEQ ID NO: 15) | 77.3 | 25.0 | 18.4 | 18.4 | 19.3 | 20.3 |
| GPRP (SEQ ID NO: 1) | 31.7 | 19.3 | 19.3 | 19.3 | 20.3 | 20.3 |
| GPRPP (SEQ ID NO: 2) | 239.7 | 60.2 | 21.2 | 18.4 | 19.3 | 19.3 |
| GPRPV (SEQ ID NO: 10) | 168.4 | 43.1 | 20.3 | 18.4 | 19.3 | |
| GPRPI (SEQ ID NO: 11) | 93.4 | 27.9 | 19.3 | 18.4 | 20.3 | |
| GPRPF (SEQ ID NO: 6) | 47.8 | 20.3 | 18.4 | 19.3 | 19.3 | |
| GPRPAG (SEQ ID NO: 20) | 195.1 | 49.7 | 20.3 | 18.4 | 19.3 | |
| GLRPG (SEQ ID NO: 22) | 21.2 | 21.2 | 21.2 | 20.3 | 21.2 | |

Test mixture III: 20 µl of clot inhibitor with thrombin
130 µl of plasma

| Concentration of clot inhibitor mg/ml | Clotting time in seconds | | | | |
|---|---|---|---|---|---|
| | 10 | 5 | 2.5 | 1.25 | 0.625 |
| Peptide amide | | | | | |
| GPRPPP (SEQ ID NO: 16) | 43.1 | 85.8 | 35.5 | 20.3 | 18.4 |
| GPRPG (SEQ ID NO: 7) | 656.8 | 104.8 | 40.2 | 19.3 | 18.4 |
| GPRPPR (SEQ ID NO: 18) | 209.3 | 70.6 | 28.8 | 19.3 | 18.4 |
| GPRPRP (SEQ ID NO: 19) | 323.3 | 77.3 | 28.8 | 18.4 | 18.4 |
| GPRPA (SEQ ID NO: 3) | 999.9 | 272.9 | 76.3 | 25.0 | 18.4 |
| GPRPD (SEQ ID NO: 12) | 101.0 | 24.1 | 18.4 | 18.4 | 17.4 |
| GPRPW (SEQ ID NO: 8) | 155.2 | 38.3 | 19.3 | 18.4 | 18.4 |
| GPRPK (SEQ ID NO: 5) | 575.1 | 114.3 | 41.2 | 20.3 | 18.4 |
| GPRP (SEQ ID NO: 1) | 926.6 | 86.7 | 22.2 | 18.4 | 18.4 |
| GPRPP (SEQ ID NO: 2) | 327.7 | 97.2 | 37.3 | 20.3 | 18.4 |
| GPRPV (SEQ ID NO: 10) | 69.7 | 109.6 | 43.1 | 20.3 | 18.4 |
| GPRPI (SEQ ID NO: 11) | 448.7 | 107.7 | 32.6 | 19.3 | 18.4 |
| GPRPF (SEQ ID NO: 6) | 261.6 | 59.2 | 20.3 | 18.4 | 18.4 |
| GPRPAG (SEQ ID NO: 20) | 22.2 | 71.6 | 45.0 | 20.3 | 18.4 |
| GLRPG (SEQ ID NO: 22) | 18.4 | 18.4 | 18.4 | 18.4 | 18.4 |

We claim:

1. A peptide amide having the formula I $$GPRP-X-NR_1-R_2 \qquad I$$

where G is the amino acid glycine, P is the amino acid proline, R is the amino acid arginine, X is an amino acid selected from the group consisting of Ala, Asp, Glu, Gly, Ile, Ser, and Val (SEQ ID NOS: 3, 12, 13, 14, 11, 15, and 10 respectively); N is nitrogen and $R_1$ and $R_2$ are identical or different and are hydrogen or a lower alkyl chain having up to 4 carbon atoms.

2. A peptide amide as claimed in claim 1, wherein X is an amino acid selected from the group Gly or Ala, and $R_1$ and $R_2$ are hydrogen.

3. A pharmaceutical composition for inhibiting fibrin/thrombin clotting having an effective amount of a peptide amide as claimed in claim 1.

4. A peptide amide as claimed in claim 1 wherein x is selected from the group consisting of Ala, Asp, Glu, Gly, Ile and Ser.

5. A peptide amide having the Formula I $$GPRP-X-NR_1-R_2 \qquad I$$

where G is the amino acid glycine, P is the amino acid proline, R is the amino acide arginine, X is an amino acid selected from the group consisting of Ala, Gly, Ile, and Val (SEQ ID NOS: 3, 14, 11, and 10, respectively); N is nitrogen and $R_1$ and $R_2$ are identical or different and are hydrogen or a lower alkyl chain having up to 4 carbon atoms.

6. The peptide amide GPRPA—$NH_2$ (SEQ ID NO: 3), GPRPS—$NH_2$ (SEQ ID NO: 4), GPRPG—$NH_2$ (SEQ ID NO: 7), GPRPV—$NH_2$ (SEQ ID NO: 10), GPRPI—$NH_2$ (SEQ ID NO: 11), GPRPD—$NH_2$ (SEQ ID NO: 12), GPRPE—$NH_2$ (SEQ ID NO: 13), GPRPG—NH(ethyl) (SEQ ID NO: 14), GPRPG—N(ethyl)$_2$ (SEQ ID NO: 14), GPRPS—NH(isopropyl) (SEQ ID NO: 15), GPRPG—NH(butyl) (SEQ ID NO: 14), GPRPPP—$NH_2$ (SEQ ID NO: 16), GPRPGG—$NH_2$ (SEQ ID NO: 17), GPRPPR—$NH_2$ (SEQ ID NO: 18), GPRPPP—NH(isopropyl) (SEQ ID NO: 16), GPRPAG—$NH_2$ (SEQ ID NO: 20) or GPRPGG—$NH_2$ (SEQ ID NO: 21).

* * * * *